(12) United States Patent
Wetzel et al.

(10) Patent No.: US 9,303,717 B2
(45) Date of Patent: Apr. 5, 2016

(54) RATE-RESPONSIVE, STRETCHABLE DEVICES

(71) Applicant: U.S. Army Research Laboratory, Adelphi, MD (US)

(72) Inventors: Eric D. Wetzel, Baltimore, MD (US); Paul T. Nenno, Murrysville, PA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 175 days.

(21) Appl. No.: 13/927,985

(22) Filed: Jun. 26, 2013

(65) Prior Publication Data
US 2014/0015176 A1    Jan. 16, 2014

Related U.S. Application Data

(60) Provisional application No. 61/670,430, filed on Jul. 11, 2012.

(51) Int. Cl.
*F16F 13/00* (2006.01)
*A61F 5/01* (2006.01)
*F16F 13/08* (2006.01)

(52) U.S. Cl.
CPC ............. *F16F 13/002* (2013.01); *A61F 5/0123* (2013.01); *F16F 13/08* (2013.01)

(58) Field of Classification Search
CPC ........ F16F 13/002; F16F 13/08; A61F 5/0123
USPC ....................... 267/69; 188/267, 267.2, 266.1
See application file for complete search history.

(56) References Cited

U.S. PATENT DOCUMENTS

| 5,712,011 | A  | * | 1/1998  | McMahon et al. ........... 428/36.9 |
| 7,402,147 | B1 |   | 7/2008  | Allen |
| 2006/0260027 | A1 | * | 11/2006 | Rhodes et al. .................... 2/421 |

OTHER PUBLICATIONS

C Fischer, et al., "Dynamic properties of sandwich structures with integrated shear-thickening fluids," Smart Mater. Struct. 15 (2006) 1467-1475.
X Z Zhang, W H Li, and X L Gong, "The rheology of shear thickening fluid (STF) and the dynamic performance of an STF-filled damper," Smart Mater. Struct. 17 (2008) 035027.
(Continued)

*Primary Examiner* — Melanie Torres Williams
(74) *Attorney, Agent, or Firm* — Eric B. Compton

(57) ABSTRACT

Rate-dependent, elastically-deformable devices according to various embodiments can be stretched and recovered at low elongation rates. Yet they become stiff and resistive to stretching at high elongation rates. In one embodiment, a rate-dependent, elastically-deformable device includes an elastically-deformable confinement member; one or more filaments placed inside the elastically-deformable confinement member; and a fluid that substantially fills the remaining volume inside the elastically-deformable confinement member. The resistance force to extension of the device is designed to increase as the extension rate of the device increases. At low elongation rates the filaments can readily slide past each other. At high elongation rates, the fluid transforms to a less flowable material that greatly increases the force and energy required for elongation; or transforms to a non-flowable material that resists elongation. The devices thus can be stretched and recovered at low elongation rates, but become extremely stiff and resistive to stretching at high elongation rates.

25 Claims, 9 Drawing Sheets

Initial, Undeformed State of Device

(56) References Cited

OTHER PUBLICATIONS

Norman J. Wagner and John F. Brady "Shear thickening in colloidal dispersions," Phys. Today 62, 27 (2009).
M. A. Dawson et al., "The Dynamic Compressive Response of an Open-Cell Foam Impregnated With a Non-Newtonian Fluid," Journal of Applied Mechanics, 76 (2009), p. 061011.
M Soutrenon and V Michaud, "Impact properties of shear thickening fluid impregnated foams," Smart Mater. Struct. 23 (2014) 035022.
Paul T Nenno and Eric D Wetzel, "Design and properties of a rate-dependent 'dynamic ligament' containing shear thickening fluid," Smart Mater. Struct. 23 (2014) 125019.

Darpa, "Warrior Web to Prevent Injury, Reduce Effects of Load," Oct. 5, 2011. (Available at: http://www.darpa.mil/NewsEvents/Releases/2011/10/05.aspx).
Darpa: Defence Sciences Office, "Warrior Web," Nov. 16, 2011. (Available at: http://www.darpa.mil/Our_Work/DSO/Programs/Warrior_Web.aspx).
E.D. Wetzel, Y. S. Lee, R. G. Egres, K. M. Kirkwood, J. E. Kirkwood, and N. J. Wagner. "The effect of rheological parameters on the ballistic properties of shear thickening fluid (STF)-Kevlar composites." Proceedings of NUMIFORM 2004. Columbus, OH. p. 288-293. Jun. 13-17, 2004.

* cited by examiner

Initial, Undeformed State
of Device

State After Low-Rate
Elongation of Device

State After High-Rate
Elongation of Device

RATE-RESPONSIVE, STRETCHABLE DEVICES

CROSS REFERENCE TO RELATED APPLICATION(S)

This application claims the benefit of U.S. Provisional Patent Application No. 61/670,430 filed Jul. 11, 2012, herein incorporated by reference in its entirety for all purposes.

GOVERNMENT INTEREST

The invention described herein may be manufactured, used and licensed by or for the U.S. Government without the payment of royalties thereon.

BACKGROUND OF THE INVENTION

1. Field

Embodiments of the present invention generally relate to elastic or resilient mechanical devices, and in particular to rate-dependent, elastically-deformable devices.

2. Description of Related Art

Springs and elastic bands are used in a range of mechanical and assistive devices to provide resilient elastic force. For example, knee braces typically made out of stretchable fabrics or external linkages permit some motion to the knee, but do not effectively restrict rapid motions that can lead to injury. Many joint injuries are associated with rapid twisting and translations of limbs and joints, such as slipping, stepping in a hole, landing from a jump, or planting a foot while changing direction. In fact, musculoskeletal injuries (i.e. twisted knees, ankles, and back injuries) account for 82% of lost time among military personnel. Many of these injuries are associated with dynamic activities such as airdrops or jumping out of vehicles. These injuries may be further exacerbated by the approximately 100 lbs of weight in additional equipment that a soldier or warfighter may be wearing or carrying.

SUMMARY OF THE INVENTION

Rate-dependent, elastically-deformable devices according to various embodiments can be stretched and recovered at low elongation rates. Yet they become stiff and resistive to stretching at high rates.

In one embodiment, the rate-dependent, elastically-deformable device includes an elastically-deformable confinement member; one or more filaments placed inside the elastically-deformable confinement member; and a fluid that substantially fills the remaining volume inside the elastically-deformable confinement member. The resistance force to extension of the device is designed and configured to increase as the extension or elongation rate of the device increases. At low rates the filaments can readily slide past each other. At high rates, the fluid transforms to a less flowable material that greatly increases the force and energy required for increased elongation; or transforms to a non-flowable material that resists further elongation.

The elastically-deformable confinement member may be formed of rubber, silicone, elastomer, fluoroelastomer, urethane, natural latex, synthetic latex, polymer, or thermoplastic elastomer. In some embodiments, the elastically-deformable confinement member is a stretchable tube, which may be approximately 0.01-100 mm in diameter in an initial undeformed state. Moreover, the elastically-deformable confinement member may include spiral wound material or folded material in order to facilitate elastic deformation. The elastically-deformable confinement member might further include material or one or more layers or additives to prevent puncturing by the enclosed filaments. The fluid is contained inside the elastically-deformable confinement member by crimps, plugs, melted ends, heat-crimped ends, glue and/or adhesives. Ends of the elastically-deformable confinement member may be able to engage and/or may further include an end effector for attaching to an object external to the device. The end effector may include, for instance, a crimp, clamp, spring clip, threaded fastener, snap-on fastener, glue and/or adhesive.

The one or more filaments may be formed of steel, polymer, glass, or carbon. They can be approximately 0.001-10 mm in diameter, and can be monofilament or multifilament, twisted, untwisted or braided. In some embodiments, the one or more filaments are flat, flexible elements. Also, the filaments may include a helical shape; a wavy shape; a square shape; a triangular shape; a sawtooth shape; or a sinusoidal shape; and/or at least one crimp, barb, bump, or ridge, to further encourage interaction during shear. Ends of the one or more filaments can be modified to inhibit puncturing through the confinement member, where the filament end modifications may include rigid, smooth balls; compression sleeves; soft coatings; filament loops; low-friction coatings; and guide bushings or washers. At least one end of the one or more filaments may be attached to the confinement member in some embodiments.

The fluid may be a non-Newtonian fluid, in some embodiments, such as a shear thickening fluid (STF). In some instances, the fluid may comprise a suspension including solid particles in a liquid, with the particles being composed of polymers, ceramics, metals silica, alumina, titania, clay, calcium carbonate and the liquid being water, an oil, a polymeric liquid, a glycol, a fluorofluid, or glycerin. In other embodiments, the fluid may be an electrorheological fluid, and the device is further configured to provide an electric field to the fluid, or the fluid may be a magnetorheological fluid, and the device is further configured to provide a magnetic field to the fluid.

According to other embodiments, an apparatus may be formed of one or more of rate-dependent, elastically-deformable devices. The apparatus may be configured as an orthotic device, safety equipment, sporting/athletic equipment, robotic assembly, or mechanical assembly.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. The drawings are not to scale unless so stated. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

FIG. 1(a) shows the device at an initial, undeformed state, FIG. 1(b) shows the device in a state after slow elongation; and FIG. 1(c) shows the device in a state after rapid elongation.

FIG. 2(a) shows a plot of force versus displacement, and FIG. 2(b) shows a plot of force versus time, for different elongation rates.

FIG. 3(a) shows an elastic knee brace with small diameter devices arrayed on the knee brace to provide targeted reinforcement, and FIG. 3(b) shows a hinged knee brace in which a larger diameter device resists high rate bending.

FIG. 4(a) shows a situation of a person walking normal over an inclined surface, and FIG. 4(b) shows a situation of a quick, abrupt drop onto an inclined surface.

FIG. 5(a) shows the device coupling between the helmet and shoulder portions of a protective vest, and FIG. 5(b) shows the device coupling between the helmet and shoulder portions of clothing.

FIG. 6(a) shows end plugs used for sealing the devices along with thin, stiff ribbons, FIG. 6(b) shows compression sleeves placed on the ends of the internal filaments to prevent puncture of the filament ends through the walls of the tubing, FIG. 6(c) shows a plurality of compression sleeves attached to the filament to increase the surface area of the filament and/or to increase fluid shearing, FIG. 6(d) shows elastic recovery components connected to the end of the opposite filaments which serves to decrease recovery time for the device to return to its initial undeformed state, and FIG. 6(e) shows an rigid element used to limit ultimate extension of the device.

DETAILED DESCRIPTION

Rate-dependent, elastically-deformable devices according to various embodiments can be stretched and recovered at low elongation rates. Yet they become stiff and resistive to stretching at high elongation rates.

Figure 1A:
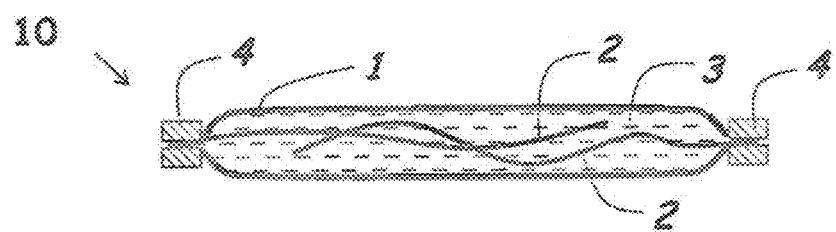
FIGS. 1(a)-1(c) illustrate schematics of one rate-dependent, elastically-deformable device, and its operation, according to one embodiment, where
Figure 1B:
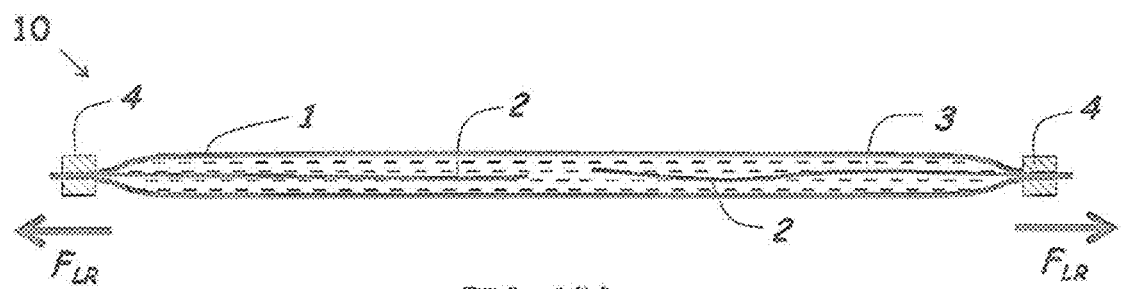
Figure 1C:
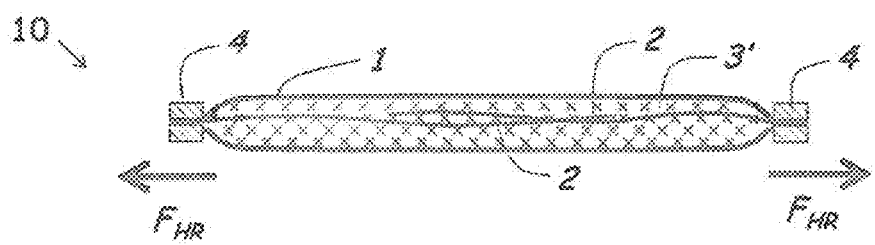

FIGS. 1(a)-1(c) illustrates one rate-dependent, elastically-deformable device 10 and its operation in accordance with one embodiment of the present invention. These figures show a cross-sectional cut-away view along the length of the device 10. In general, the rate-dependent, elastically-deformable device 10 includes an elastically-deformable confinement member 1 which houses one or more filaments 2, as well as a fluid 3 which substantially fills the remainder interior volume of the confinement member 1. The fluid 3 is sealed within the confinement member 1 by a crimp seal 4. The device 10 is configured to elongate or otherwise stretch by the application of an external tensile force applied at its ends.

The resistance force to extension of the device 1 is designed and configured to increase as the rate of extension or rate of elongation of the device 10 increases. The extension rate or elongation rate of the device can be expressed, for example, as a relative elongation of the device as a function of time or the speed/velocity of the device at one of its ends which displaces with respect to the other. These rates may be measured in units such as meters/sec, inches/sec, mm/sec, etc., although the extension or elongation rate might also be expressed as a dimensionless strain value (e.g., elongation of the device normalized by the initial device length) as a function of time. This may be expressed in units of $s^{-1}$. Other conventions might also be used for extension or elongation rates. It should also be appreciated that the terms low-rate elongation and high-rate elongation as used herein may be relative to a particular embodiment or application. Put another way, what may be a low rate of elongation for one application may not be a low rate of elongation for another application. Similarly, what may be a high rate of elongation for one application may not be a high rate of elongation for a different application. Thus, a key feature of the innovative technology is the ability to judiciously tailor or otherwise configure the elongation rate response of individual devices to any particular application.

FIG. 1(a) shows the device 10 in an initial undeformed state with no external tensile force applied. The elastically-deformable confinement member 1 may be formed of rubber, silicone, elastomer, fluoroelastomer (such as sold under the tradename Viton®), urethane, natural latex, synthetic latex, thermoplastic elastomer, polymer, or the like, which generally are elastic and resilient and capable of confining a fluid therein. Latex may be stretchier than some of the other materials, but is also more porous to certain materials. The fluid 3 may be confined to interior of the elastically-deformable confinement member 1 by crimps, plugs, melted (heat-crimped) ends, glues or adhesives (such as thermoplastic or thermoset resins) provided at the ends of the elastically-deformable confinement member 1.

In one embodiment, the elastically-deformable confinement member 1 may be formed of a stretchable elastic tube. The use of an elastic tube enables flexibility of the device 10 in multiple directions. For some applications, the tube may have an inner diameter of about 0.01-100 mm, or more preferably 0.1-10 mm in an initial undeformed state. The tube may generally have a circular cross-sectional shape for many applications, but it should be appreciated that other cross-sectional shapes are also possible, such as rectangular, square, hexagonal, etc.

The elastically-deformable confinement member 1 might also be formed into a planar shape, for example, formed by sealing the edges of two sheets of elastomeric materials to form an elastomeric membrane. This elastomeric body could be shaped like a square sheet, round membrane, or arbitrarily-shaped body. An array of filaments 2 could be enclosed in this elastomeric body, and with the filaments aligned in parallel, orthogonally, or in any arbitrary combination of in-plane orientations. The precise shape of the body and the orientation of the filaments 2 will be dictated by the application. It should be appreciated that other stretchable configurations are also possible. For instance, the outer confinement member 1 could be formed (or partially formed along its length) of spiral wound or folded material which can elongate linearly when stretched, like a bellows, for example.

To prevent puncturing by the enclosed filaments 2, the elastically-deformable confinement member 1 may formed of a reasonable thickness whether formed of one layer or formed of multiple layers. Wire mesh or fibers might further be incorporated into the walls of the elastically-deformable confinement member 1 for this purpose. In addition, to enhance sliding of the filaments 2 relative to the elastically-deformable confinement member 1, interior surfaces of the elastically-deformable confinement member 1 may be further provided with a low-friction coating or layer of material, such as Teflon®.

The filaments 2 may include be formed of wire, cable, ribbon, band, thread, cord or the like, of steel, polymer, glass, carbon or other appropriate material for this purpose. The filaments 2 may be flexible to provide flexibility of the device 10 as well, but need not be flexible for all embodiments. The filaments 2 may be monofilament or multifilament, twisted, untwisted or braided. In one embodiment, the filaments are flat, flexible elements, such as ribbons. And a pair of ribbons may be provided with ones of the pair being connected to opposite ends of the elastically-deformable confinement member 1 in some instances. The ribbons may be formed of strip-shaped materials formed of nylon or metal, for example. There are certain advantages to using flat ribbons including (i) there is more shear area between a pair of ribbons, as compared to a pair of round cables, so that higher force resistance to elongation is possible, and (ii) ribbons can be stiffer than cables so the ribbon-based device recovers from its stretched state (i.e. relaxes) faster than a cable-based device.

In the preferred embodiment, one end of each and every filament 2 may be coupled to the elastically-deformable confinement member 1, preferably at or near its ends. To this end, the filaments 2 may be mechanically and/or adhesively coupled to the confinement member 1. For mechanical attachment, a crimp, clamp, spring clip, threaded fastener, snap-on fastener, stitch, and/or the like may be used. FIGS. 1(a)-1(c) illustrate the device 10 having filaments 2 coupled to the ends of the elastically-deformable confinement member 1 by a crimp seal 4. For adhesive coupling, various thermosetting or thermoplastic (heat-setting) glues and adhesive may be used, including hot-melt, urethane, silicone, epoxy, acrylate, or the like, as some examples. If the filaments 2 are themselves readily stretchable or elastic, both of their ends could be coupled to opposite ends of the elastically-deformable confinement member 1 so as to stretch along with the elastically-deformable confinement member 1.

In another embodiment, one or more filaments 2 in the device could be unconstrained to the confinement member 1. These filaments would be freely floating in the device, but would provide some mechanical or viscous coupling to other filaments 2 during device extension.

End effectors (not shown) may be coupled to or otherwise provide mounting points on the ends of member 1 which may used to connect the device 10 to other systems such as mechanical linkages. Depending of the application, the end effector mounting may be permanent or readily removable. Such end effectors may include, for instance, threaded attachment (e.g., via screws or eyehooks), clips, clasps, buckles, snaps, buttons, straps, knots, stitches/stitching, staples, hooked fasteners, clamps, cotter pins, nails, glue/adhesives, or the like.

For some applications, the filaments 2 may have an outer diameter of about 0.01-10 mm in diameter, or more preferably 0.1-1 mm. Smaller and larger filaments might also be used for other applications. In order to inhibit their puncturing through the outer confinement member 1, the filaments 2, and particularly their ends, may be modified. For example, filament modifications may include rigid, smooth balls; soft coatings; filament loops; low-friction coatings; guide bushings or washers; chamfering; or compression sleeves. Grinding, sanding, or soldering may also be used to blunt or dull the tips the filaments 2 to inhibit puncturing through the confinement member 1.

Generally speaking, the filaments 2 should have some degree of stiffness for effective operation of the device 10. For example, the filaments 2 may be "push-pull" cables. By push-pull, it is meant that the filament 2 can readily be pushed and pulled through the fluid 3. Most filaments are sufficient to be pulled through a fluid because the drag between the filament and fluid tends to keep the filament in a state of tension generally unfurling the filament. However, when pushed through the fluid, the viscosity of the fluid tends to keep the filament in a state of compression. Thus, a very thin flexible thread might not be an effective filament because it may buckle, ball-up, or tangle-up due to compressive forces between the filament and the fluid when the device retracts. To increase shearing of the fluid 3, the filaments 2 may further include one or more crimps, barb, ridges, waved surfaces (e.g., square, triangular, sawtooth or sinusoidal shaped surfaces), etc. Also, the filaments 2 might be arranged in a helical (or "corkscrew") arrangement to encourage entanglement.

One important aspect of the invention is that the resistance force to extension of the device changes, and in particular, increases as the extension rate of the device increases through the use the fluid 3. The fluid 3 may be selected so as to change its rheological properties as the rate of extension of the device changes. For example, the device 10 may be designed so as to have a predetermined threshold rate of extension in which such a change occurs. Thus, at low rates below the threshold, the filaments 2 can readily slide through the fluid 3 and/or past each other. Yet at high rates above the threshold, the fluid 3 transforms to a more rigid material or higher viscosity fluid which greatly reduces or prevents movement of the filaments 2 through the fluid 3 and producing a stiff linear element. Put another way, the device 10 may be thought of as being easily stretchable at low elongation rates, but "stiffens" or "locks up" (i.e., rigidly resists or substantially prevents any further deformation) when pulled quickly at high elongation rates.

The fluid 3 substantially fills the remaining volume inside the elastically-deformable confinement member 1 once the filaments 2 are installed therein. The fluid 3 may be a Newtonian or non-Newtonian fluid. Newtonian fluids have a viscosity that will change with temperature, but do not change with the strain rate. By contrast, non-Newtonian fluids have a viscosity that changes with the strain rate which may enable devices to be more tailored for certain operational performance.

In some embodiment, fluid 3 may be a shear thickening fluids (STFs). STFs, one type of non-Newtonian fluid, are materials that flow like a liquid at low deformation rates, but become highly resistant to flow at high deformation rates. Exemplary thickening fluids which may be used in accordance with the embodiments of the present invention are disclosed in Norman J. Wagner and John F. Brady "Shear thickening in colloidal dispersions," Phys. Today 62, 27 (2009), herein incorporated by reference. Stretching the device 10 at low rates does not transition the STF, and the filaments 2 are free to move through the fluid 3 and slide past each other. If, instead, the device 10 is pulled quickly, high shear rates develop between the filaments and the STF material hardens, binding the filaments together and providing high resistance to elongation or a stiff, generally unstretchable device state. Relaxation of the force induces the STF to return to a flowable state, and the device once again becomes stretchable. By using a Newtonian fluid, rather than a true shear thickening fluid, one can get a useful rate-dependent response, although the rate-dependence of the response is not nearly as severe or drastic as devices containing an STF. The ideal rate-dependent response of a device depends on the application. For some applications, severe stiffening may be desirable to "lock" the device and prevent further motion. In other applications, a "locked" response may create an undesirably severe effect; instead, a device that is still extensible, but at considerably higher elongation forces, might be more desirable. The properties of fluid 3 can be tailored to provide the desired device response.

In some embodiments, the fluid 3 may be a suspension of solid particles in a liquid (which may also be referred to as a carrier fluid or carrier liquid). For example, the suspension may be formed of colloidal particles generally nano-sized (i.e. 1-1000 nm). Colloidal refers to the fact that the particles are intact solid particles, they may not dissolve in the liquid, and they are generally stabilized in the liquid so that they do not agglomerate, settle, or float to the surface of the liquid system over short periods of time (i.e. they are stable for days, weeks, or longer). However, devices 10 may be constructed with a fluid 3 that is a suspension of larger size solid particles (i.e. 10-1000 µm, or even larger), which do not dissolve in the liquid and are generally stable in the liquid too. In these devices, the fluid is technically not a colloid. The term "suspension" as used herein is intended to encompass both colloids and suspensions of larger size solid particles in a liquid.

Depending on the type of particles and liquid, and the desired non-Newtonian response, the solid particles may constitute 10-70% by volume of the fluid 3; more preferably, the solid particles constitute 30-60% by volume of the fluid 3. For examples, a preferred volume fraction for spherical particles is around 50% by volume; a preferred volume fraction for high aspect ratio precipitated calcium carbonate particle may be as low as 35% The liquid could be water, oil, a polymeric liquid, a glycol, a fluorofluid, or glycerin, for example. The colloidal particles may be composed of ceramics, polymers (such as poly(methyl methacrylate) (PMMA) or polystyrene), or metals. Or, they may comprise of silica, alumina, titania, clay, precipitated calcium carbonate, or ground calcium carbonate. It is believed that precipitated calcium carbonate is more likely to be stable than ground calcium carbonate in some instances. One or more additional additives might also be included in the fluid 3 which function as stabilizers, emulsifiers, surfactants, pigments, etc. The fluid 3 may also include gels, gums, and putties.

In other embodiments, the fluid 3 may be an electrorheological fluid, or a magnetorheological fluid. Electrorheological fluids include a suspension of extremely fine non-conducting particles (e.g., up to 50 micrometers diameter) in an electrically insulating fluid. The viscosity of these fluids can change reversibly (e.g., an order of up to 100,000) in response to an electric field. Magnetorheological fluids include a suspension of fine ferromagnetic particles in a liquid. When subjected to a magnetic field, the fluid greatly increases its viscosity, to the point of becoming a viscoelastic solid. In the case of using an electrorheological fluid, a voltage may be applied to the fluid 3 by using a voltage-generating device with opposite electrodes attached to filaments at opposite ends of the device; thus creating an electric field across the fluid 3 that would trigger a thickening response in the fluid. Similarly, in the case of using a magnetorheological fluid, a magnetic-field-generating device provided in the vicinity of the fluid 3 (for example, using an electromagnet) generates a magnetic field to the fluid 3 such that the fluid 3 can increase in viscosity or transition to a non-flowable state. Suitable microcontrollers, which may include known feedback or feedforward control algorithms, may be further provided to control the voltage-generating device and magnetic-field-generating device thus providing a desired fluid response.

When the device 10 is subjected to an external tensile force, the elastically-deformable confinement member 1 elongates, and the one or more filaments 2 are pulled or dragged through the fluid 3 as it stretches. The relevant movement of the filaments 2 through the fluid 3 creates shearing flow(s) in the fluid 3. Some shearing flow may also be created by relevant movement of the fluid 3 and the interior surface(s) of the elastically-deformable confinement member 1 and/or within the fluid 3 itself. The shearing flow of the fluid 3 creates a force within the device 10 which tends to resist the external tensile force that is elongating the elastically-deformable confinement member 1.

In general, the resistive force due to the shearing flow of the fluid 3 is largely dependent on the speed or rate of elongation/stretching of the elastically-deformable confinement member 1, the surface area of the filaments 2, and/or the spacing of the filaments 2 between one another and the interior surface(s) of the elastically-deformable confinement member 1. Other factors may also influence the resistive force, such the cross-sectional shape of the elastically-deformable confinement member 1, the shape of the filaments 2, and/or the viscosity of the fluid 3, for instance.

FIG. 1(a) shows the rate-dependent, elastically deformable device 10 in an undeformed state. The elastically-deformable confinement member 1 here is in an initial, undeformed state.

As illustrated in FIG. 1(b), stretching the device 10 with an external tensile force $F_{LR}$ in an attempt to impose low-rate elongation does not create sufficient resistance force in the device 10, such that the filaments 2 are free to readily be pulled through the fluid 3 and/or slide past each other. Here, the elastically-deformable confinement member 1 has been stretched and the filaments 2 have been pulled and straightened somewhat and slid past each other. The fluid 3 remains in a flowable state similar to that of the device 10 in its initial undeformed state. Upon gradual release of the external tensile force $F_{LR}$, the elastically-deformable confinement member 1 tends to return to its initial undeformed shape and length as shown in FIG. 1(a).

On the other hand, stretching the device 10 with external tensile force $F_{HR}$ in an attempt to impose high-rate elongation, as illustrated in FIG. 1(c), changes the operable characteristics of the elastically-deformable device 10. For instance, if the device 10 is pulled quickly and elongates at a high rate, high shearing rates develop between the elastically-deformable confinement member 1, the filaments 2 and the fluid 3. The high shearing rates cause the fluid 3 to generate a high resistance force in the device 10, preventing the filaments 2 from readily sliding through the fluid 3 and/or past each other. The elastically-deformable confinement member 1 has stretched a small amount, and the filaments 2 have straightened slightly. Due to the high shearing of the fluid 3, the fluid 3 has now transformed into a more rigid-state material 3'. The filaments 2 are no longer free to readily slide past one another. This results in the device 10 transitioning to a device that is highly resistant to elongation, or becomes so resistant to elongation so as to become unstretchable. The device 10 will remain in the stiffened state as long as force is being applied to the ends of the device. If the force is relaxed, the fluid 3' will return to a flowable state like fluid 3, and the device 10 will gradually reduce in length back to the initial, undeformed state of the material shown in FIG. 1(a).

Figure 2:
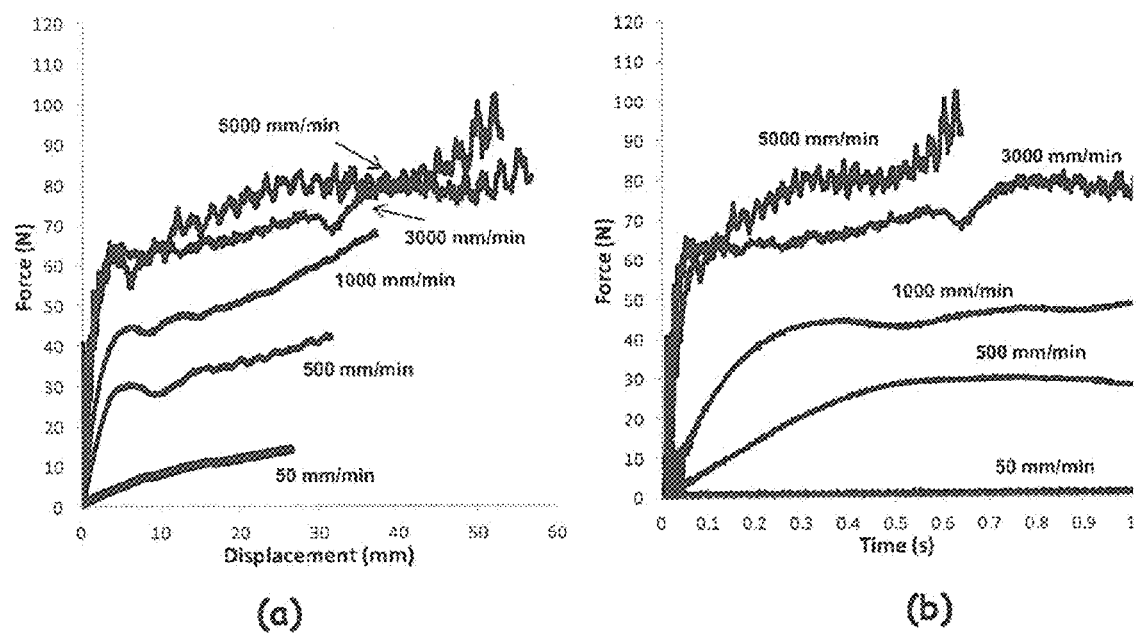
FIGS. 2(a)-2(b) illustrate experimental measurements of force versus displacement for one rate-dependent, elastically-deformable device pulled at different elongation rates, demonstrating the rate-dependent resistance to extension, where

FIGS. 2(a)-2(b) show experimental force measurements during elongation of a prototype device stretched at different rates. The elongation rates were 50 mm/min, 500 mm/min, 1,000 mm/mm, 3,000 mm/min and 5,000 mm/min. The device gage length in these experiments was 152 mm, so these deformation rates correspond to strain rates of 0.0055, 0.055, 0.11, 0.33, and 0.55 $s^{-1}$, respectively. FIG. 2(a) shows a plot of force versus displacement, and FIG. 2(b) shows a plot of force versus time, for these elongation rates.

The force versus displacement plot FIG. 2(a) demonstrates the rate-sensitive response of the device. The liquid here was a STF which was formulated by blending 450-nm-diameter silica and ethylene glycol (EG) at a mass ratio of 1.92 g silica: 1 g EG. The STF was dispersed using a rolling jar mixer over a period of 24 hours. The STF was then placed inside a 6.35-mm-ID, 7.9375-mm-OD Viton® tube with nylon end caps and 0.794-mm-diameter stainless steel wire rope with compression sleeves on the end. The tubing was filled with shear thickening fluid by partially clamping one end of the tubing with surgical tubing forceps while slowly pouring the fluid in until the fluid reached the surgical forceps. In some cases, it was helpful to apply low amounts of heat using a heat gun or to inject the fluid using a 3-mL syringe. The surgical forceps were removed and then the tubing was plugged at one end using the nylon plugs with attached wires described above. At this point, the tube was gently massaged to push air bubbles to the top of the tube and more fluid was added in order to fill the void space previously occupied by the air bubbles. Afterwards, the second nylon plug was inserted into the tubing.

The force versus time plot FIG. 2(b) shows that the devices respond very rapidly, with the high rate plateau force reached in less than 100 ms after force application. This rapid response means that there would be very little lag time between application of high elongation rate, and transformation of the device to a more resistive state.

As apparent, at the low elongation rates, the device provides very little resistance to stretching. One the other hand, as elongation rate increases, the resistance to deformation (force values during extension) increases. Comparing the highest rate response to the lowest rate response at 100 ms, the resistive force at high rate is approximately 100× higher than the resistive force at low rate. These particular embodiments of the device show a resistive force that peaks and then plateaus, which could be a beneficial feature of a device. For example, the long plateau force indicates high energy absorption during elongation. Also note that if the device is elongated at high rates, but the available elongation force is less than the plateau force, the device would essentially feel unstretchable and provide a rigid response. Other devices can be engineered with considerably higher resistive forces, and resistive forces that do not plateau but reach a limiting displacement beyond which further elongation would require exceedingly high forces.

The device tested was designed to provide much higher resistance to elongation as the elongation rate increases. But it was not designed to rigidly lock-up at high rates of elongation (rather, some elongation continued at higher rates of elongation just at much smaller degree). The device nonetheless still appeared to lock-up if the force applied is less than the plateau force. While rigid locking-up of the device may be useful for some applications, for other applications a rigid locking effect would be too severe a response, and a higher elongation force is a preferred response.

According to various embodiments of the present invention, one or more rate-dependent, elastically-deformable devices may be incorporated into various devices and apparatuses to provide rate-dependent operational performance. For example, in some embodiments, one or more rate-dependent, elastically-deformable devices may be incorporated into an apparatus such as an orthotic device to create rate dependent braces. Exemplary orthotic device which may be benefited in the manner may include, for example, head and helmet braces, knee braces, ankle braces, back braces, neck braces, wrist braces, slings, and other orthotic devices. The rate-dependent, elastically-deformable devices may also be provided in other wearable equipment, such as shoes, boots, headgear, belts, harnesses, or the like. This technology presents a new approach and, thus orthotic devices that can provide higher resistance to motion during higher speed events which a soldier or athlete may encounter. These new and improved devices will be more effective at resisting unplanned loads and preventing injuries. Many joint injuries associated with rapid twisting and translations of limbs and joints, such as slipping, stepping in a hole, landing from a jump, or planting a foot while changing direction may be prevented. In other embodiments, one or more rate-dependent, elastically-deformable devices may be incorporated into safety equipment, sporting/athletic equipment and goods, robotics, restraints (e.g., seat-belts) and mechanical assemblies. According, various applications, such as, linkages, vehicle suspension systems, robotics, "strapping" (e.g., bungee-type cords, self-tightening straps, etc.) clothing and woven textiles may be benefited. One device might be used as a replacement for a simple Velcro® or an elastic strap.

Figure 3:
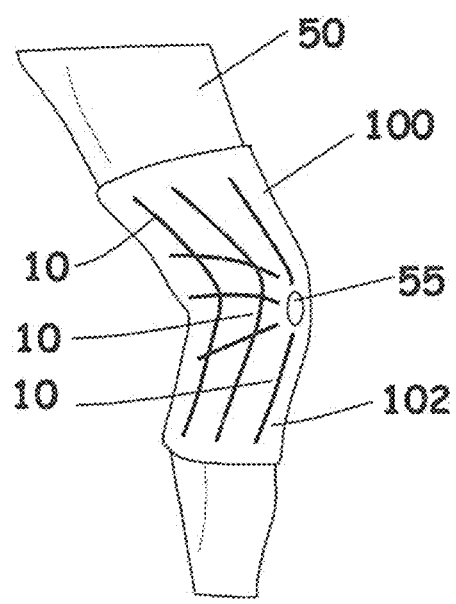
FIGS. 3(a)-3(b) illustrate two knee brace including rate-dependent, elastically-deformable devices, where
Figure 3:
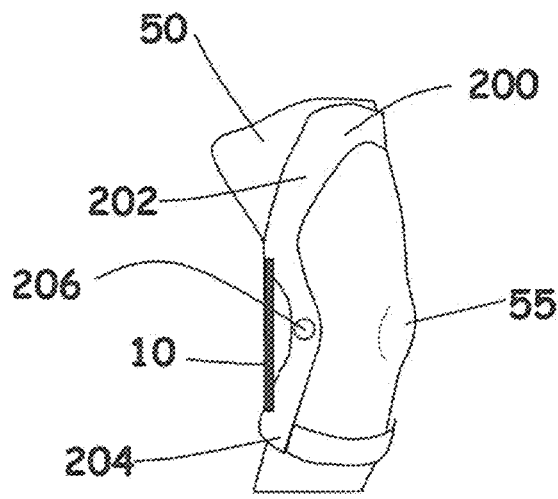
Figure 4:
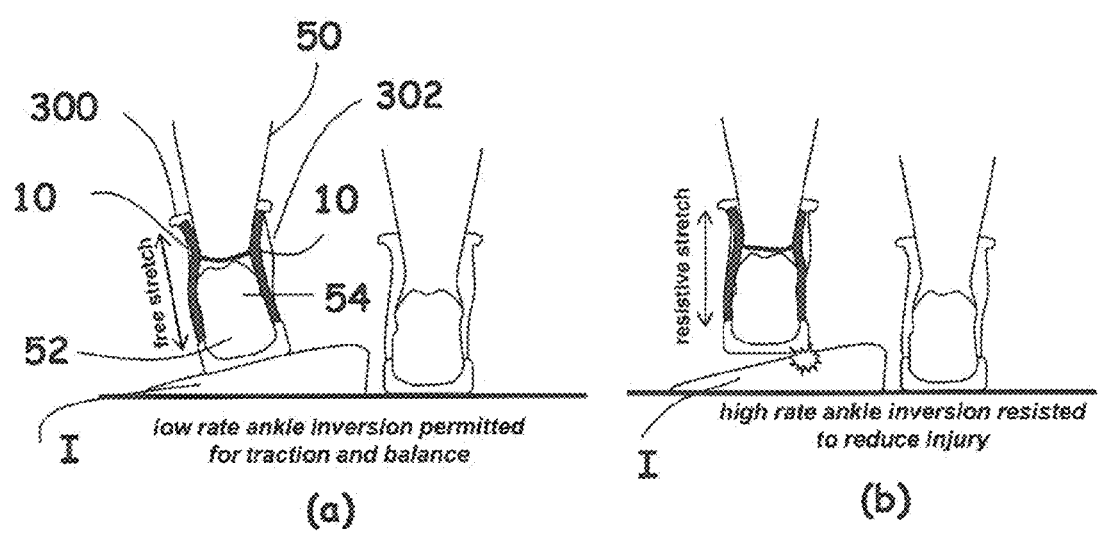
FIGS. 4(a)-4(b) illustrate an ankle brace including rate-dependent, elastically-deformable devices, and its operation, where
Figure 5:
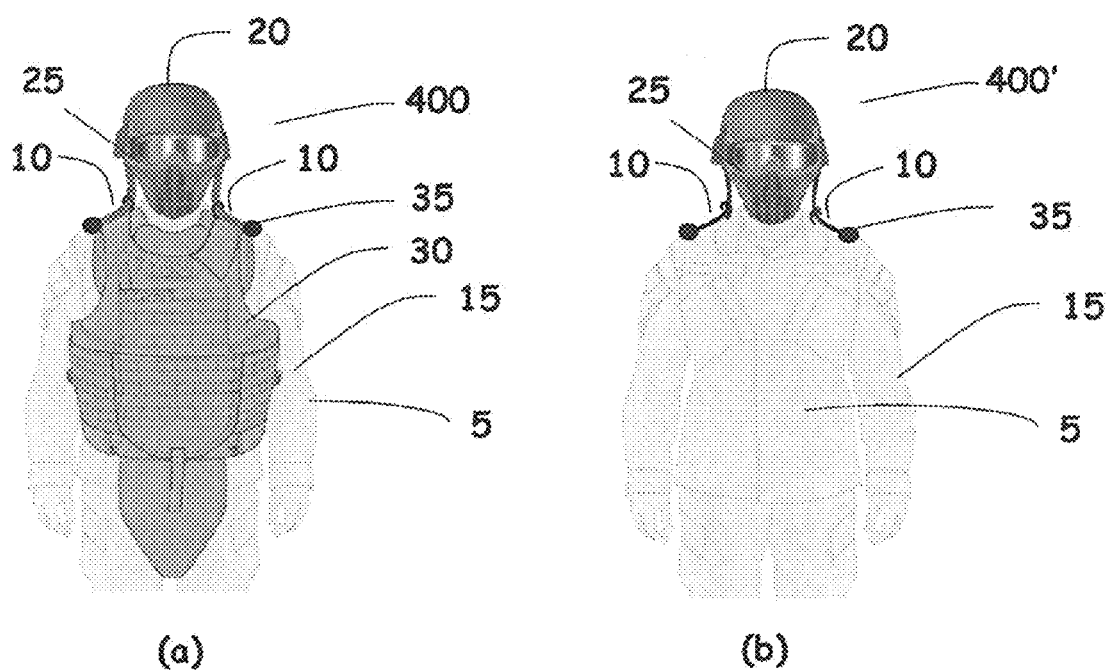
FIGS. 5(a)-5(b) illustrate a head and neck restraint device including rate-dependent, elastically-deformable devices, where

FIGS. 3-5 show examples of various orthotic devices according to embodiments of the present invention. In FIGS. 3(a)-3(b), the orthotic devices are knee braces which are configured to be worn on a person's leg 50 on the knee 55 to provide increase support and/or stability for the knee 55. The precise number of elongational devices 10 that are incorporated into the knee braces, and the orientation of these devices relative to knee physiology or desired kinesiology for a given activity or injury risk, could be tailored to a particular application. The knee braces are designed to permit normal walking and other activities, but stiffen and resist deformation during high rate events, like landing from a jump. Moreover, the knee braces provide rate-dependent operational performance not found in conventional braces.

FIG. 3(a) shows an elastic knee brace 100 according to one embodiment. The knee brace 100 includes multiple rate-dependent, elastically-deformable devices 10 that are fastened to, bonded to, woven into, and/ or otherwise attached to the body 102 of the knee brace 100. The body 102 may be formed of a conventional elastic fabric textile, such as sold under the tradename Spandex®. Or the body 102 may be formed of a rigid or semi-rigid material which comports to the curvature of the leg 50 or foot 52 as generally known. When worn, the body 102 snugly engages the leg 50 and knee 55 and holds the knee brace 100 in place. Adjustment straps (not shown) having buckles or hook and loop type (e.g., Velcro®) fastening may be further included to better couple the brace 100 to the leg 50 and knee 55. To facilitate incorporation into the fabric of the body 102, the devices 10 may have a small outer diameter, such as 0.1-10 mm.

FIG. 3(b) shows a hinged knee brace 200 according to another embodiment. The knee brace 200 body includes an upper portion 202 worn above the knee 55 and a lower portion 204 worn below the knee 55. The upper and lower portions 202, 204 are coupled with a pivot 206 to provide hinged movement of the brace 200 at the knee 55.

The upper and lower portions 202, 204 may be formed of a conventional elastic fabric textile. Or they may be formed of a rigid or semi-rigid material which comports to the curvature of the leg 50 and knee 55 as generally known. When worn, the upper and lower portions 202, 204 of the brace 200 snugly engage the knee 55 and holds the knee brace 200 in place on the person's leg 50. Adjustment straps (not shown) having buckles or hook and loop type (e.g., Velcro®) fastening may be further included to better couple the brace 200 to the leg 50 and knee 55.

The knee brace 200 further include one or more rate-dependent, elastically-deformable devices 10 which couple to the upper and lower portions 202, 204 of the brace 200. As shown, one rate-dependent, elastically-deformable device 10 externally couples those elements behind in the rear of the knee 55. Because of the greater forces the device 10 may be subject to in this orientation, it may have a large diameter, such as 1-20 mm. The device(s) 10 stretches freely during normal motion of the hinged knee brace 200, but becomes rigid during high rate motions that may cause injury.

The lengths, positions, number, orientations and/or operational characteristics of the devices 10 in the knee braces 100 and 200 are strategically designed to provide optimal support. The devices 10 incorporated into the braces 100 or 200 may have different characteristics. As shown in FIGS. 3(a) and 3(b), the rate-dependent, elastically-deformable device(s) 10 may be positioned in a generally parallel orientation parallel to the length of the leg 50 in both of these knee brace embodiments. However, the devices 10 may be additionally or alternatively oriented generally orthogonally to the length of the leg 50, and/or at some angle thereto. Also, the devices 10 might further be oriented in a "criss-cross shape" or "X-shape" to provide greater lateral support to the knee 55. Other configurations are also possible. Under normal walking conditions, the elements of the devices 10 deform passively and do not resist motion. Under high loading rate, potentially injurious conditions, such as a knee hyperextension or knee twist during slippage, the devices become rigid and greatly limit or preferably prevent further motion of the knee 55.

FIGS. 4(a)-4(b) show an ankle brace 300 and its operation, according to an embodiment. The ankle brace 300 includes multiple rate-dependent, elastically-deformable devices 10 that are fastened to, bonded to, woven into, and/ or otherwise attached to the body 302 of the brace 300.

The body 302 may be formed of a conventional elastic fabric textile. Or the body 302 may be formed of rigid or semi-rigid material which comports to the curvature of the leg 50, foot 52 or ankle 54 as generally known. When worn, the body 302 snugly engages the leg 50, foot 52 and ankle 54 and holds the ankle brace 300 in place. Adjustment straps (not shown) having buckles or hook and loop type (e.g., Velcro®) fastening may be further included to better couple the brace 300 to the leg 50, foot 52 and ankle 54. These devices 10 enable low rate extension but prevent higher rates of extension and rotation of the ankle brace 300.

FIG. 4(a) shows a situation of a person walking normal over an inclined surface I. In this situation, the person's foot 52 (on the left) needs to rotate slightly with respect to the person's leg 50 for traction and balance. In this situation, the ankle brace 300 is configured to permit a low rate of inversion of the ankle 54 and foot 52 which is typically expected for walking During the normal gait cycle, the foot both pronates and supinates. Pronation is a combination of three ankle movements, abduction, eversion, and dorsiflexion, while supination is combination of adduction, inversion, and planar flexion. When the foot hits the ground, the ankle pronates to absorb the shock, and when it pushes off, the ankle supinates.

FIG. 4(b) shows a situation of a quick, abrupt drop onto an inclined surface I. It is noted that alike elements to those in FIG. 4(a) are shown here, and will be referenced. Typically, in this situation, the person is not expecting this drop. This may occur for example when one inadvertently steps off a curb. And, because the person is not expecting the drop, the high rate of ankle inversion associated with the landing onto the incline surface I ordinarily (without the aid of the ankle brace 300) may cause injury to the person, such as an ankle sprain, or worse yet, possibly a break. It is noted that 70-80% of typical ankle sprains are caused by ankle inversion, whereas a smaller percentage is caused by ankle eversion. But, by wearing ankle brace 300, the ankle brace 300 advantageously resists the high rate of ankle inversion to reduce injury in this situation.

FIGS. 5(a)-5(b) show a head and neck restraint device 400 according to an embodiment. The person 5 shown here may be a soldier or warfighter wearing military equipment, such clothing 15, a helmet 20, a facemask 25 (e.g., having goggles and face guard), and protective vest 30 (shown in FIG. 5(a) only).

The head and neck restraint device 400 couples between to person's head and shoulders. As shown in FIG. 5(a), the device 400 couples between the helmet 20 and shoulder portions of the protective vest 30 via mounting points 35. Or, as shown in FIG. 5(b), head and neck restraint device 400' couples between the helmet 20 and shoulder portions of the clothing 15 via mounting points 35. The mounting points 35 may include clips, clasps, buckles, snaps, buttons, straps, knots, stitches, hooked fasteners, clamps, or other end effectors, for example. The device 400 further includes one or more rate-dependent, elastically-deformable device(s) 10. A pair of devices 10 is shown in the figures here positioned axially, one on each side of the person's head. This design is not to be considered limiting; other embodiments can be envisioned that use more devices, different orientations, and different fixturing. For instance, multiple devices 10 might be positioned axial around the entire neck in an orthotic device similar to a neck brace. Also, one or more devices 10 may be provide in a radial orientation, additionally or alternatively, to resist head turning or lifting motion at high rates also.

During normal operation, the devices 10 are free to stretch and do not resist head motion. Under high rate events, such as a blast event or a secondary impact when a soldier is thrown into a wall or vehicle interior, the devices 10 become stiff and resist extension. Under the latter conditions, loads to the helmet 20 are transmitted directly to the shoulders, rather than to the head and neck. By reducing head and neck loads, the risk of injury is significantly reduced. A similar head- and neck-protective device is further envisioned for contact sports applications, such as for football, hockey or lacrosse helmets in order to reduce the likelihood of concussions during impact.

FIGS. 6(a)-(e) show rate-dependent, elastically-deformable device(s) 10' according to other embodiments of the invention. These figures show a cross-sectional cut-away view along the length of the device(s) 10'. The device(s) 10' here are shown in their initial undeformed state, but are configured to elongate or otherwise stretch by the application of an external tensile force through their ends, similarly to as shown in FIGS. 1(a)-1(c).

Figure 6A:
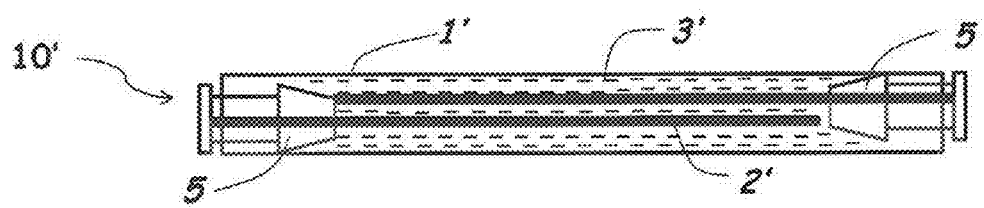
FIGS. 6(a)-6(e) illustrate various other rate-dependent, elastically-deformable devices embodiments, where

As shown in FIG. 6(a), the rate-dependent, elastically-deformable device 10' includes an elastically-deformable confinement member 1' which houses one or more filaments 2', as well as a fluid 3 which substantially fills the remainder interior volume of the confinement member 1'. Filaments 2' may be formed of are flexible, stiff filaments, such as nylon ribbons. They may have a rectangular cross-section in some embodiments. To confine fluid 3' inside the elastically-deformable confinement member 1', plugs 5 may be used. The elastically-deformable confinement member 1' may be formed of tubing may have overall length of about 6-in and an outer diameter of about 5/16-in. The filaments 2' may have a length of 4.75-in. The plug 5 may have a diameter of about 0.3175-in to provide a frictional or interference fit with the confinement material tubing 1'. The plugs 5 seal the ends of outer confinement member 1 so as to maintain the liquid 3 therein. Preferably, this is a hermetic seal to prevent evaporation and/or outgassing, as well as prevent the ingress and egress of dirt, debris and contaminants which could contaminate the liquid 3'and impede operation of the device 10'. The plugs 5 also may serve as an attachment point for the filaments 2'; for example, the plugs may be hollow in the barbed section, so that one end of the filament can be placed in the hollow section, then adhesive can be poured into the plug to permanently attach the filament end to the nylon plug. Furthermore, the outside end of the plug 5 provides a convenient mounting or attachment point for other hardware (e.g., end effectors) for coupling the device 10 to other bodies.

Figure 6B:
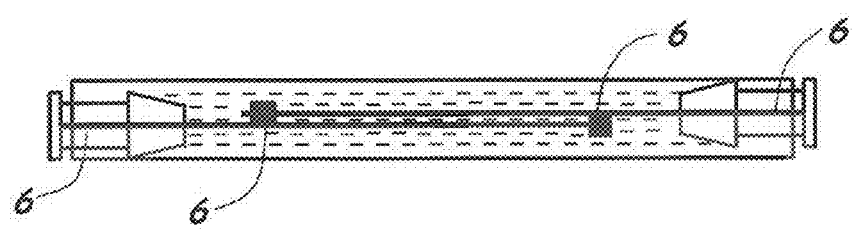
Figure 6C:
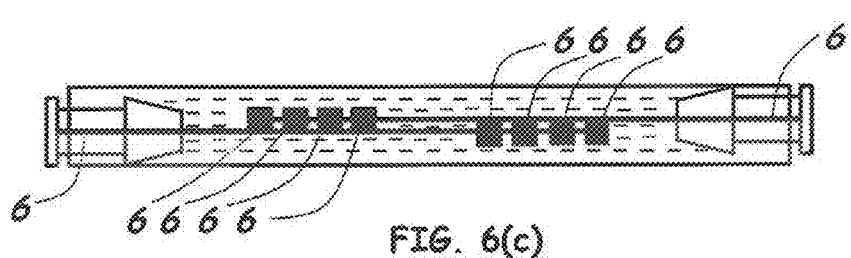
Figure 6D:
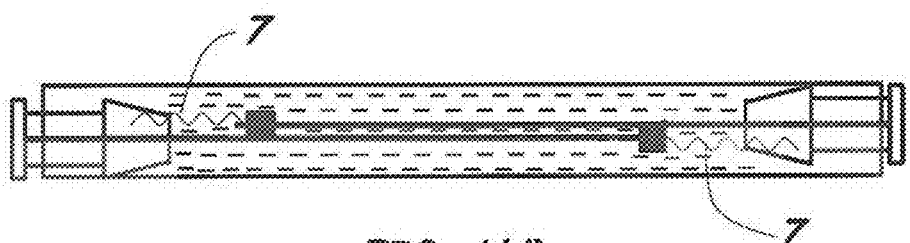

FIG. 6(b) shows compression sleeves 6 placed on the ends of the internal filaments to prevent puncture of the filament 2' ends through the walls of the tubing 1'. FIG. 6(c) shows a plurality of compression sleeves 6 placed not only at the ends but along the length of the filaments 2' to increase the surface area of the filament 2' and/or to increase shearing of the fluid 3'. FIG. 6(d) shows elastic recovery components 7 connected to the end of the opposite filaments 2', which serves to decrease recovery time for the device 10' to return to its initial undeformed state. The elastic recovery components 7 may be springs or elastic filaments, for example.

Figure 6E:
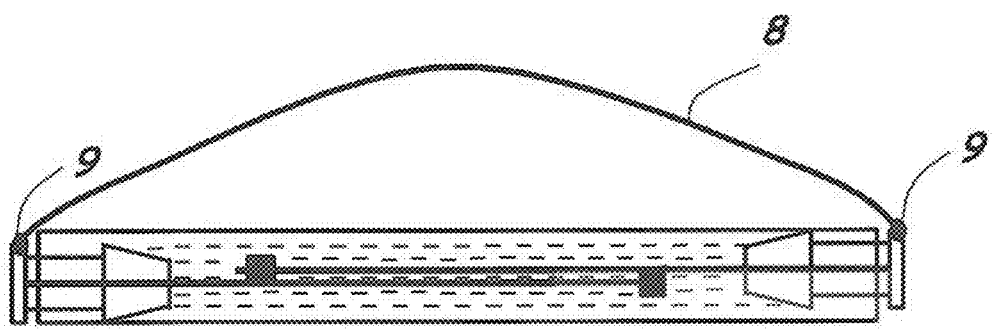

FIG. 6(e) shows an external rigid filament 8 used to limit ultimate extension of the device (i.e. to serve as a "hard stop"). The ends of the hard stop 8 may be attached to the plug 5 at location 9 by adhesive, for example.

Figure 7:
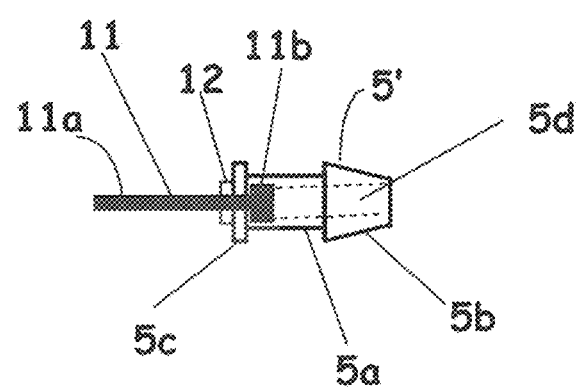
FIG. 7 illustrates an end plug of one rate-dependent, elastically-deformable device according to one embodiment.

FIG. 7 shows a modified embodiment of the plug 5' illustrated in FIGS. 6(a)-6(e). The plug 5' may include a central body portion 5a, a tapering enlarged diameter front portion 5b, and reared flange portion 5c. The front portion 5b, also known as a barbed portion, is adapted to be inserted into the ends of the elastically-deformable confinement member 1' to confine fluid 3 therein. The enlarged diameter being slightly larger than that of the elastically-deformable confinement member 1' may facilitate a friction or interference fit, for instance. Glue or adhesive may be further provided to additionally couple the plug 5' to the elastically-deformable confinement member 1'. In some instances, the central body portion 5a may include "flats" on its exterior sidewalls to resist or limit rotational movement of the plug 5' when it is inserted into the elastically-deformable confinement member 1'. An axial bore 5d is provided through the body portion 5a of the plug. The diameter of the bore 5d in front of the flanged front portion 5c is slightly larger than the diameter of the head 11b of the threaded fastener 11. However, the diameter of the bore 5d through the flanged portion 5c is slightly larger than the diameter of the threaded portion 11a, but slightly less than the diameter of the head 11b. As such, the threaded portion 11a of the fastener can be inserted into the axial bore from the front side to the rear side, with the head of the fastener engaging an inner wall of the bore 5d at the flange where the diameter of the bore changes. The nut 12 can be threaded onto the threaded portions 11a of the threaded fastener from the rear of the plug so as to trap and fix the threaded fastener 11 to the plug 5'.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

We claim:

1. A rate-dependent, elastically-deformable device comprising:
    an elastically-deformable confinement member;
    one or more filaments placed inside the elastically-deformable confinement member;
    a fluid that substantially fills the remaining volume inside the elastically-deformable confinement member; and
    one or more barbed plugs inserted into the ends of the elastically-deformable confinement member to contain the fluid and which are mechanically attached to at least one end of one filament,
    wherein the resistance force to extension of the device increases as the extension rate of the device increases.

2. The device of claim 1, wherein the elastically-deformable confinement member is formed of rubber, silicone, elastomer, fluoroelastomer, urethane, natural latex, synthetic latex, polymer, or thermoplastic elastomer.

3. The device of claim 1, wherein the elastically-deformable confinement member comprises a stretchable tube.

4. The device of claim 1, wherein the elastically-deformable confinement member comprises spiral wound material or folded material in order to facilitate elastic deformation.

5. The device of claim 1, wherein the elastically-deformable confinement member comprises material or one or more layers or additives to prevent puncturing by the enclosed filaments.

6. The device of claim 1, wherein the fluid is contained inside the elastically-deformable confinement member by crimps, plugs, melted ends, heat-crimped ends, glue and/or adhesives.

7. The device of claim 1, wherein ends of the elastically-deformable confinement member comprise an end effector for attaching to an object external to the device.

8. The device of claim 7, wherein the end effector comprises: a crimp, clamp, spring clip, threaded fastener, snap-on fastener, glue and/or adhesive.

9. The device of claim 1, wherein the one or more filaments are monofilament or multifilament, twisted, untwisted or braided.

10. The device of claim 1, wherein the one or more filaments are flat, flexible elements.

11. The device of claim 1, wherein the one or more filaments include a helical shape; a wavy shape; a square shape; a triangular shape; a sawtooth shape; or a sinusoidal shape; and/or at least one crimp, barb, bump, or ridge, to further encourage interaction during shear.

12. The device of claim 1, wherein the ends of the one or more filaments are modified to inhibit puncturing through the confinement member.

13. The device of claim 12, wherein the filament end modifications include rigid, smooth balls; compression sleeves; soft coatings; filament loops; low-friction coatings; and guide bushings or washers.

14. The device of claim 1, wherein at least one end of the one or more filaments is attached to the confinement member.

15. The device of claim 1, wherein the fluid comprises a non-Newtonian fluid.

16. The device of claim 15, wherein the non-Newtonian fluid is a shear thickening fluid (STF).

17. The device of claim 16, wherein the fluid comprises a suspension including solid particles in a liquid.

18. The device of claim 17, wherein the particles are composed of polymers, ceramics, metals, silica, alumina, titania, clay, or calcium carbonate.

19. The device of claim 17, wherein the liquid comprises water, an oil, a polymeric liquid, a glycol, a fluorofluid, or glycerin.

20. The device of claim 1, wherein the fluid is a Newtonian fluid.

21. An apparatus comprising: one or more of rate-dependent, elastically-deformable devices of claim 1, wherein the one or more of rate-dependent, elastically-deformable devices mechanically couple the head and shoulders of an individual wearing the apparatus.

22. A rate-dependent, elastically-deformable device comprising:
   an elastically-deformable confinement member;
   one or more filaments placed inside the elastically-deformable confinement member; and
   a fluid that substantially fills the remaining volume inside the elastically-deformable confinement member, wherein the fluid comprises an electrorheological fluid, and the device is configured to provide an electric field to the fluid,
   wherein the resistance force to extension of the device increases as the extension rate of the device increases.

23. A rate-dependent, elastically-deformable device comprising:
   an elastically-deformable confinement member;
   one or more filaments placed inside the elastically-deformable confinement member; and
   a fluid that substantially fills the remaining volume inside the elastically-deformable confinement member, wherein the fluid comprises a magnetorheological fluid, and the device is configured to provide a magnetic field to the fluid,
   wherein the resistance force to extension of the device increases as the extension rate of the device increases.

24. A rate-dependent, elastically-deformable device comprising:
   an elastically-deformable confinement member;
   one or more filaments placed inside the elastically-deformable confinement member, wherein the one or more filaments are unattached to the confinement member; and
   a fluid that substantially fills the remaining volume inside the elastically-deformable confinement member,
   wherein the resistance force to extension of the device increases as the extension rate of the device increases.

25. A rate-dependent, elastically-deformable device comprising:
   an elastically-deformable confinement member;
   one or more filaments placed inside the elastically-deformable confinement member; and
   a fluid that substantially fills the remaining volume inside the elastically-deformable confinement member, wherein the fluid comprises a non-Newtonian, shear thickening fluid (STF) comprising a suspension including solid particles in a liquid, wherein the solid particles are non-spherical,
   wherein the resistance force to extension of the device increases as the extension rate of the device increases.

* * * * *